(12) United States Patent
Loos et al.

(10) Patent No.: US 6,579,309 B1
(45) Date of Patent: Jun. 17, 2003

(54) STENT FOR VESSEL BRANCHINGS

(75) Inventors: Hartmut Loos, Overijse (BE); Curt Kranz, Berlin (DE)

(73) Assignee: Biotronik Mess-und Therapiegerate GmbH & Co. Ingenieurburo Berlin, Berlin (DE)

( * ) Notice: Subject to any disclaimer, the term of this patent is extended or adjusted under 35 U.S.C. 154(b) by 43 days.

(21) Appl. No.: 09/633,363

(22) Filed: Aug. 7, 2000

(30) Foreign Application Priority Data

Aug. 6, 1999 (DE) .......................................... 199 38 377

(51) Int. Cl.$^7$ .................................................. A61F 2/06
(52) U.S. Cl. ...................... 623/1.16; 623/1.15; 606/191; 606/194
(58) Field of Search ............................ 623/23.64, 23.7, 623/1.1, 1.15, 1.16, 1.3, 1.32, 1.35; 606/191, 192, 194, 195, 198

(56) References Cited

U.S. PATENT DOCUMENTS

| 6,210,429 B1 | * | 4/2001 | Vardi et al. | 606/153 |
| 6,325,826 B1 | * | 12/2001 | Vardi et al. | 623/1.35 |
| 6,494,905 B1 | * | 12/2002 | Zedler et al. | 623/1.11 |

FOREIGN PATENT DOCUMENTS

| EP | 0 732 088 | 9/1996 |
| EP | 0 897 700 | 2/1999 |
| EP | 0 904 745 | 3/1999 |
| EP | 0 904 745 A2 | 3/1999 |
| EP | 0 904 745 A3 | 1/2000 |
| WO | WO 97/41803 | 11/1997 |
| WO | WO 97/45073 | 12/1997 |
| WO | WO 98/18404 | 5/1998 |
| WO | WO 99/15109 | 4/1999 |

OTHER PUBLICATIONS

International Search Report for EP 00 25 0261.

* cited by examiner

Primary Examiner—David J. Isabella
Assistant Examiner—Urmi Chattopadhyay
(74) Attorney, Agent, or Firm—Christie, Parker & Hale, LLP

(57) ABSTRACT

A stent, in particular a coronary stent, for implantation in the region of vessel branchings, comprising a tubular casing with a proximal and a distal end, wherein in the implanted condition the proximal end is arranged in proximal relationship with the vessel branching and the distal end is arranged in distal relationship with the vessel branching, and at least one branching portion, which is arranged at the periphery of the casing and which is provided to open a passage into the branching-off branch of the vessel and which in the implanted condition is arranged in the region of the vessel branching, wherein the branching portion includes at least one first support element, which is provided for supporting the vessel transition and which can be pivoted substantially radially out of the peripheral surface and which extends from a first direction into the branching portion, and wherein the branching portion includes at least one second support element, which is provided for supporting the vessel transition and which can be pivoted substantially radially out of the peripheral surface and which extends into the branching portion from a second direction which is substantially opposite to the first direction.

8 Claims, 4 Drawing Sheets

STENT FOR VESSEL BRANCHINGS

CROSS REFERENCE TO RELATED APPLICATION

This application claims priority of German patent application number 19938377.4, filed Aug. 6, 1999.

FIELD OF INVENTION

The invention concerns a stent, and, in particular a coronary stent for implantation in the region of vessel branching& having a tubular casing with a proximal end and a distal end.

BACKGROUND OF MENTION

A stent is an intraluminal support element. Such a support element serves to support the wall of a generally constricted vessel in the human or animal body in order to hold the vessel in a dilated position. Stents of that kind are frequently used, as so-called coronary stents, in the region of constricted coronary blood vessels.

In that respect, known stents generally consist of a tubular casing with a proximal end and a distal end, which is moved in a non-expanded condition to the location to be dilated in the vessel. When it is in the desired position the casing is suitably expanded, radially, to a diameter at which the vessel wall therearound is dilated to the desired diameter. Thereafter, the stent of its own accord remains in that condition in order to hold the vessel in a permanently dilated state.

It is frequently necessary for the stent to be implanted in the region of vessel branchings. Stents are known for that purpose, in such stents, in the implanted condition, the proximal end is arranged in proximal relationship with the vessel branching and the distal end is arranged in distal relationship with the vessel branching. Such stents also have at least one branching portion which is arranged at the periphery of the casing and which is disposed in the implanted condition in the region of the vessel branching. Upon implantation, that branching portion is generally deformed in such a way that it opens a passage into the branching-off branch of the vessel.

Such a stent is known, for example, from European patent application No. EP 0 904 745 A2. In that stent, to open the passage into the branching-off branch of the vessel, one or more first support elements, which are in mutually adjoining relationship in the peripheral direction of the stent and which extend from a first direction, in this case the direction of one end of the casing into the branching portion, are pivoted substantially radially by plastic deformation out of the peripheral surface of the casing into the branching-off branch of the vessel.

However, the problem which arises in such a stent design is that the vessel transition of the branching configuration is inadequately supported. The vessel transition is on the one hand a highly sensitive region of the vessel, which is subjected to a particular loading when a stent is implanted only in one branch of the vessel. On the other hand, maintenance of its natural geometry is an aspect of significance from points of view relating to flow dynamics therein, as it is only in that way that the normal circulation can be restored, and, for example, the only way formation of deposits due to detrimental flow conditions can be avoided. Admittedly, the first support element of the known stent already permits a certain amount of support for the vessel transition. That, however, is only at one side and therefore under some circumstances it results in an unwanted unnatural deformation and loading of the vessel transition.

Therefore the object of the present invention is to provide a start of the kind set forth in the opening part of this specification, for providing improved support for the vessel transition in the region of a vessel branching.

SUMMARY OF THE INVENTION

The present invention is directed to a stent of the kind set forth in the opening part of this specification, where the branching portion includes at least one second support element which is provided for supporting the vessel transition, and which can be pivoted substantially radially out of the peripheral surface, and which extends from a second direction different from the first direction into the branching portion.

The invention embraces the technical teaching that an improved supporting action for the vessel transition is achieved if the branching portion includes at least one second support element which is provided for supporting the vessel transition, and which can be pivoted substantially radially out of the peripheral surface, and which extends into the branching portion from a direction which is in a substantially opposite relationship to the first. In this arrangement, the two support elements can be pivoted into the branching-off branch of the vessel in the manner of a saloon door, and thereby support the vessel transition from two oppositely disposed points. This ensures that the loadings are more uniformly applied to the delicate vessel transition, as occur for example precisely in the case of movements of the vessel transversely with respect to the plane of the branching, with such movements being strong movements in the region of the coronary vessels.

In one embodiment, the first direction may entail any desired direction. Thus it is possible for example for the first direction to extend from the distal end of the stent parallel to the longitudinal axis thereof. It is, however, also possible for the first direction to extend in a peripheral direction of the stent.

In another embodiment, there is provided at least one third support element which is arranged adjacent to the first or second support element transversely with respect to the first direction. The support portions can be uniformly distributed and for example can extend into the branching portion from directions which are mutually displaced through 120° relative to each other. Such an arrangement ensures an even more uniform supporting effect. This supporting effect can also be additionally improved if the stent has a fourth support element, arranged transversely in relation to the first direction, in adjacent relationship with the first and second support elements. It will be appreciated, moreover, that it is also possible to provide firer respective support elements, which are arranged in adjacent relationship transversely with respect to the first direction.

In another embodiment, the first and second support elements can be arranged in such a way that in the initial condition they are in mutually adjoining relationship, transverse with respect to the first direction, that is to say they extend along each other over a given length Preferably, the second support element is arranged in substantial alignment with the first support element in the first direction- This permits simple positioning of the stent in the region of the vessel branching with a branching-off vessel branch of relatively small diameter. It is only necessary in that case for the two free ends of the support elements to be placed approximately in the center of the passage of the branching, which is possible, for example, by means of a guide wire which is passed through between the two ends.

In another embodiment of the stent according to the invention, the support elements are of an elongated configuration, whereby on the one hand simple deformation into the support position thereof is possible. On the other hand, support elements of this kind permit use thereof in vessel branchings of the most widely varying diameters in respect of the branching-off branch of the vessel. Thus, when the branching-off branch of the vessel is of relatively small diameter, only the free end region of the respective support element can be used to support the vessel transition, while when dealing with larger diameters, the support element possibly extends over its entire length into the branching-off branch of the vessel. Thus, the stent can provide a long support length and thus give a good supporting action.

In another embodiment of the invention, the support elements are formed by bar or web elements which extend substantially parallel to the first direction, and which are distinguished by particularly simple handling upon deformation thereof to assume their supporting position. In such an embodiment, the configuration of the bar or web elements in that arrangement is substantially in the manner of a hairpin, with the bend region forming the free end of the support element. This provides on the one hand a strong and stable support element, and on the other hand, with that arrangement, it is possible to adopt a particularly desirable configuration in which the limbs of the support element are connected to the casing in such a way that they move away from each other upon expansion of the stent. This results on the one hand in a stable support geometry, while on the other hand it results in support points for the wall of the vessel that are further away from each other and that are thus more uniformly distributed.

In another embodiment of the stent according to the invention, the support elements, which are in mutually adjoining relationship transverse to the first direction, are connected at their free end by way of at least one connecting element, thereby providing for support for the vessel transition over a relatively large surface area. Preferably, the connecting element is of an arcuate configuration so that, upon deformation of the support elements into their supporting position, lengthwise compensation can take place between the free ends.

In another embodiment of the invention, the support elements are of such a configuration and arrangement that in the implanted condition, with support elements which are pivoted radially out of the peripheral surface to support the vessel transition, the branching portion opens a passage in the peripheral surface, which passage is substantially adapted to the contour of the vessel transition. This ensures particularly uniform support for the transitional region.

In another embodiment of the stent according to the invention, which are particularly desirable because they are simple to fit in position, the stent has a number of branching portions. For positioning purposes, it is then generally sufficient to place any one of the branching portions in the region of the vessel branching.

In another embodiment, branching portions for passages of different dimensions are provided, which are suitable for use in the region of branching-off vessel branches of different diameters.

In another embodiment, at least a part of the branching portion is arranged in an annular region of the casing in the peripheral direction of the casing so that, for positioning a branching portion in the region of the vessel branching, the angular position of the stent only has to be changed about its longitudinal axis by a comparatively slight amount. In that respect, the amount is particularly slight if the branching portions are arranged in the annular region in an immediately mutually adjoining relationship.

The present invention further concerns a process for implanting a stent according to the invention, which is distinguished in that the support elements are pivoted radially out of the peripheral surface into the vessel branching after expansion of the casing in the manner of a saloon door by an actuating means which is moved to the branching portion. In that arrangement, the actuating means used is preferably a guide wire. Preferably in that arrangement the guide wire also serves for positioning the stent prior to expansion so that there is no need to provide or move to the stent a separate actuating means.

In another embodiment, to expand the stent use is made of a balloon catheter, which at its distal end has a balloon with a proximal chamber and a distal chamber spaced therefrom, between which chambers the guide wire forming the actuating means issues. That permits particularly fast and simple implantation of the stent.

BRIEF DESCRIPTION OF THE DRAWINGS

Other advantageous developments of the invention are characterized in the appendant claims or are set forth in greater detail hereinafter together with the description of the preferred embodiment of the invention, with reference to the drawings in which:

DETAILED DESCRIPTION OF THE INVENTION

The present invention is directed to a stent where the branching portion includes at least one second support element which is provided for supporting the vessel transition, and which can be pivoted substantially radially out of the peripheral surface, and which extends from a second direction different from the first direction into the branching portion.

Figure 1:
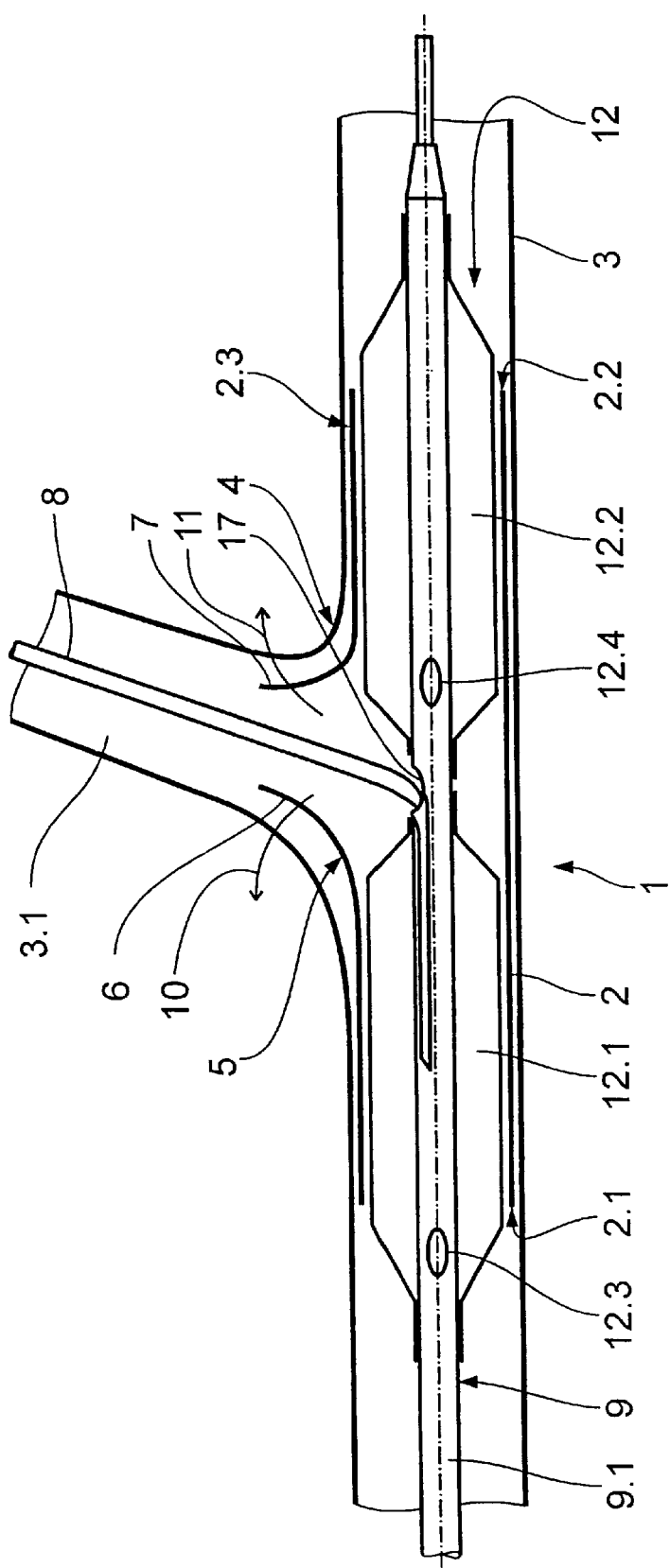
FIG. 1 is a diagrammatic view of a preferred embodiment of the stent according to the invention in the implanted condition.

FIG. 1 diagrammatically shows a stent according to the invention having a tubular casing 2 with a proximal end 2.1 and a distal end 2.2. The stent is shown in a condition of being implanted in a blood vessel 3. The stent is disposed in the region of a vessel branching 4, with its proximal end 2.1 arranged in proximal relationship with the vessel branching 4 and its distal end 2.2 arranged in distal relationship with the vessel branching 4.

The stent 1 has a branching portion 5 which in the illustrated implanted condition is arranged in the region of the vessel branching 4. To support the vessel transition 4, the branching portion 5 includes an elongated first support element 6 and an elongated second support element 7. In the initial condition (not shown here) of the stent 1 the first support element 6 and the second support element 7 are disposed in the peripheral surface 2.3 of the casing 2. In this situation the first support element 6 extends in a first direction into the branching portion 5. That first direction extends from the proximal end 2.1 of the stent 1 in parallel relationship with the longitudinal axis thereof The second support element 7 extends in a second direction which is opposite to the first direction, into the branching portion 5, that is to say from the distal end 2.2 in parallel relationship with the longitudinal axis of the stent 1.

The support elements 6 and 7 are curved radially out of the peripheral surface 2.3 into the branching-off branch 3.1 of the vessel by means of a first guide wire 8 of the balloon catheter 9, in the direction of the arrow 10 or 11 respectively, in the manner of a saloon door. In the fully implanted condition (not shown here) the first and second support elements 6 and 7 bear completely against the wall of the vessel transition 4 to support same.

In this respect, the casing 2 of the stent 1 can be designed in any known fashion. Thus, as in the illustrated embodiment, it can be formed with a plastically deformable structure, for example a known grid-like bar structure, which is deformed radially into the illustrated dilated condition by means of the balloon 12 of the balloon catheter 9, and which remains in that condition after removal of the balloon 12 in order to bold the vessel 3 permanently dilated.

It will be appreciated, however, that the casing may also be in the form of the so-called self-expanding type which, due to a previous elastic radial compression effect, is deformed of its own accord into a condition in which it holds the vessel permanently dilated.

Figure 2A:
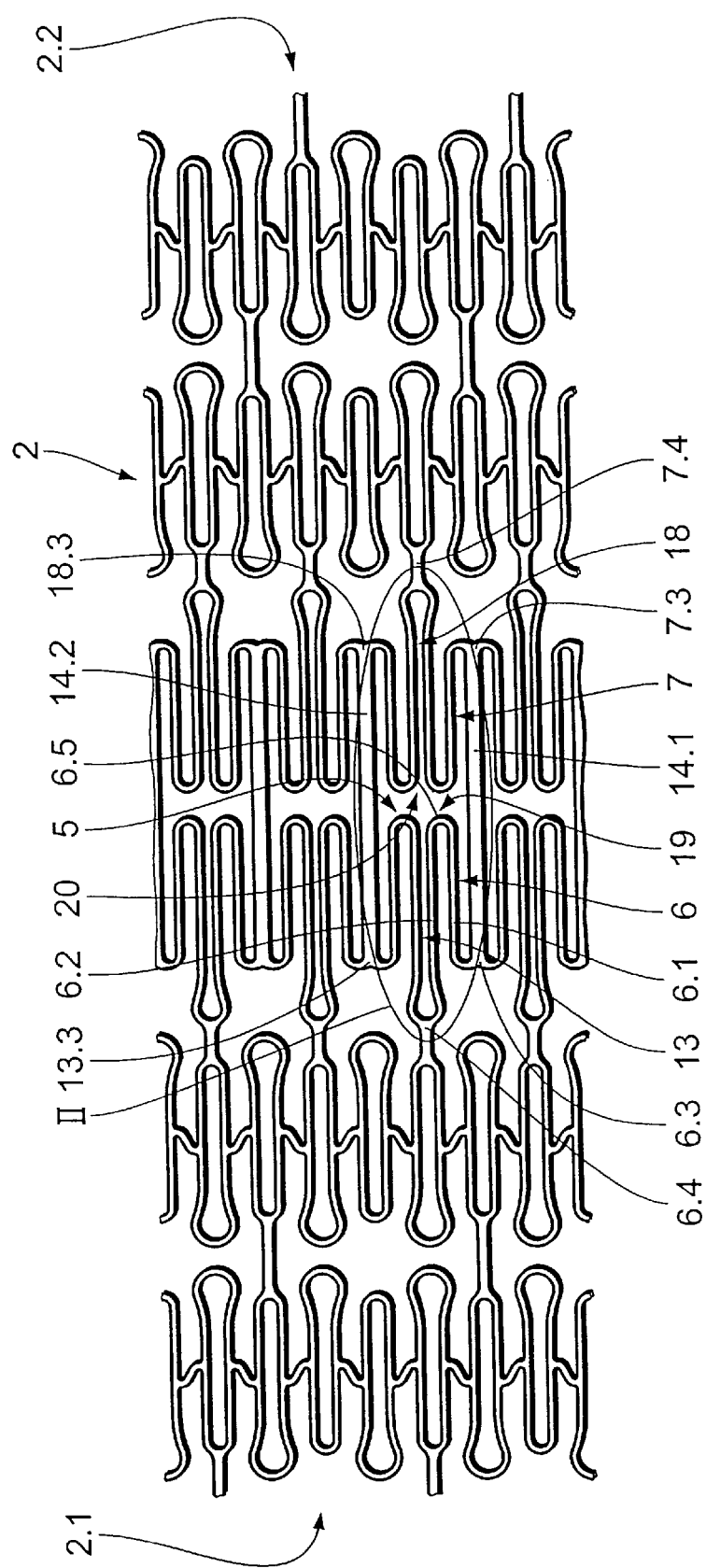
FIG. 2a is a developed view of the peripheral surface of a further embodiment of the stent according to the invention.
Figure 2B:
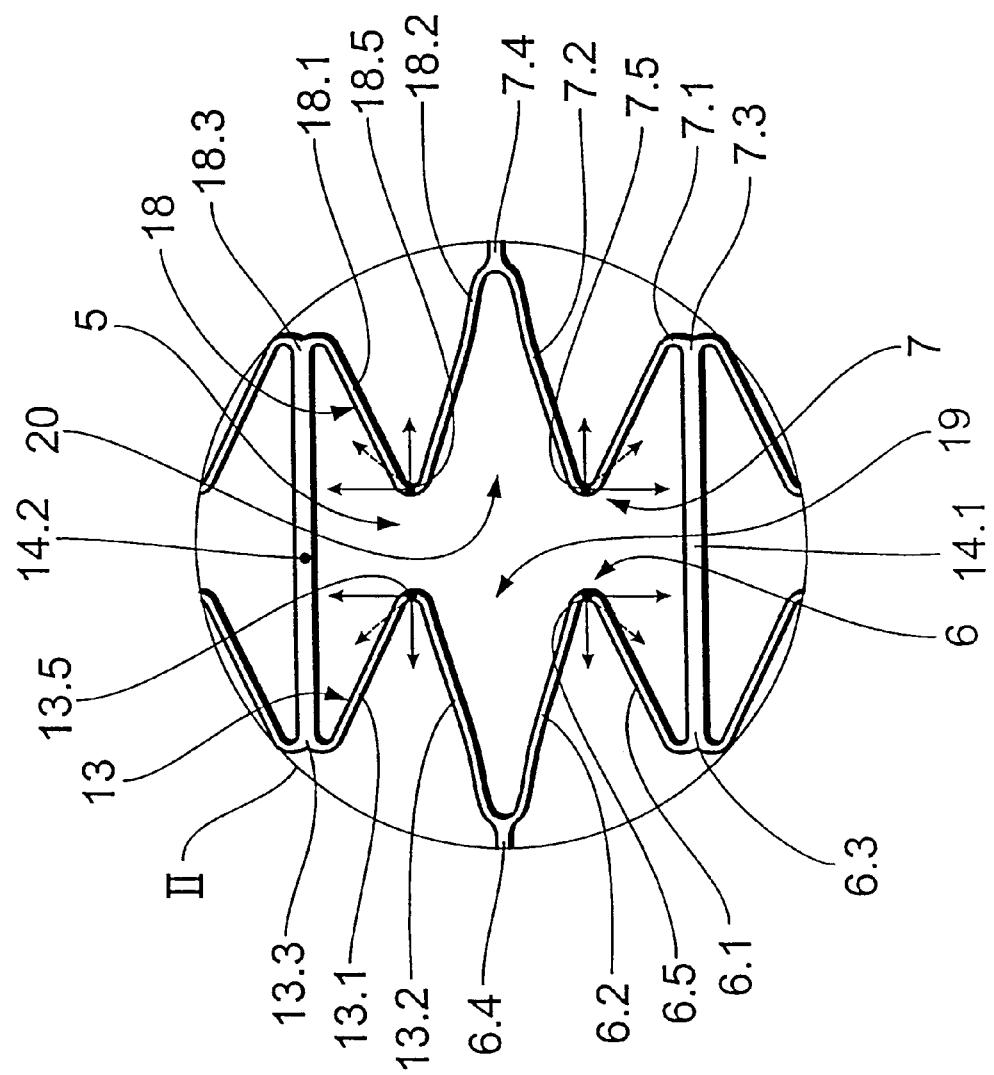
FIG. 2b is a close-up developed view of the peripheral surface of the embodiment of the stent shown in FIG. 2a and the relative motion of the support elements.

FIGS. 2a and 2b show a development of the casing 2 of the stent according to the invention as shown in FIG. 1, comprising a structure of bar-like or web-like elements. In this case, the casing 2 has a number of branching portions 5 which are in mutually adjoining relationship in the peripheral direction of the casing.

The respective branching portion 5 includes a first support element 6, and a second support element 7, which is arranged in alignment with respect thereto in the first direction, that is to say in the longitudinal direction of the casing 2, and a respective third and fourth support elements 13 and 18 respectively which are arranged adjacent to the first and second support elements 6 and 7, respectively, transverse to the first direction, that is to say in the peripheral direction of the casing 2.

Furthermore, the branching portion 5 is delimited in the peripheral direction of the casing 2 on both sides by a bar or web 14.1 and 14.2 extending in the direction of the longitudinal axis of the casing 2.

The support elements 6, 7, 13 and 18 are respectively formed by bar or web elements which extend substantially in the longitudinal direction of the casing 2, and which are configured in the manner of a hairpin. In this case, the bend region forms the free end of the respective support element 6, 7, 13, and 18, respectively.

The configuration and arrangement of the support elements 6, 7, 13, and 18 respectively will be described representatively herein by reference to the example of the support element 6, as shown most clearly in FIG. 2b. The limbs 6.1 and 6.2 of the support element 6 are connected to the bar 14.1 and to the casing 2 respectively in such a way that the connecting points 6.3 and 6.4 move away from each other upon expansion of the stent structure. In that way, on the one hand the hairpin-like support element 6 in the peripheral surface is bent open from the side remote from the bend region 6.5, thus resulting in an increase in the size of the vessel region which can be supported thereby. On the other hand, this also causes the free ends of the support elements 6 and 13 (pair 19), and 7 and 18 (pair 20) respectively to move away from each other in the peripheral direction, thus resulting in more uniform distribution of the support elements over the vessel transition which is to be supported.

As shown in FIG. 2b, the first limb 6.1, which is towards the bar 14.1 is shorter than the second limb 6.2 which is towards the adjacent support element 13 so that the connecting points 6.3 and 6.4 are spaced from each other in the longitudinal direction of the casing 2. In the implanted condition, therefore, when the support elements 6, 7, 13, and 18 are pivoted about the connecting line of the connecting points into the branching-off branch of the vessel, that opens a passage into the branching-off vessel, which passage is essentially adapted to the ellipsoidal contour of the vessel transition. This arrangement ensures uniform support for the vessel transition.

By virtue of the inclination of the connecting line between the connecting points with respect to the peripheral direction of the casing, the support elements 6, 7, 13, and 18, which are pivoted into the branching-off branch of the vessel extend inclinedly with respect to the longitudinal direction of the branching-off branch of the vessel, whereby the support for the wall of the vessel by means of the support elements 6, 7, 13, and 18 advantageously extends in the region of the vessel transition over a relatively large peripheral region of the branching-off branch of the vessel. In that respect, the angle of inclination with respect to the longitudinal axis of the branching-off branch of the vessel and thus the supported peripheral region is increased, the greater the degree of inclination of the connecting line between the connecting points relative to the peripheral direction.

Figure 3:
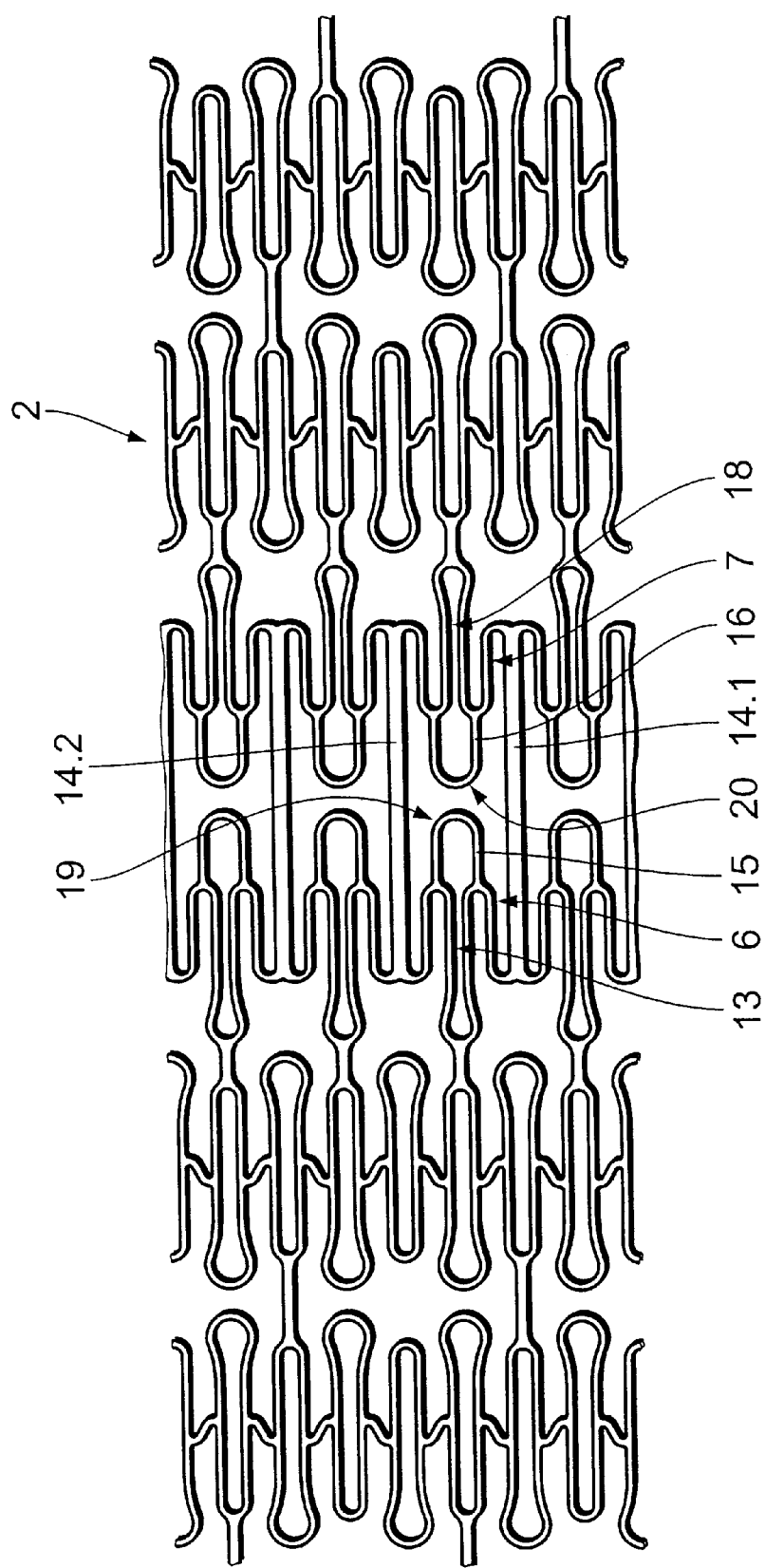
FIG. 3 is a developed view of the peripheral surface of another embodiment of the stent according to the invention.

FIG. 3 shows a development of the peripheral surface of a further embodiment of a stent according to the invention which is substantially the same as the structure shown in FIGS. 2a and 2b, so that here only the differences will be discussed.

The difference in this respect is that the free ends of the support elements 6 and 13 are connected by way of a bar-like arcuate connecting element 15 and the free ends of the support elements 7 and 18 are connected by way of a bar-like arcuate connecting element 16. In that case, the arcuate connecting elements 15 and 16, respectively are of an arcuate length which is sufficient to compensate for a variation in spacing between the free ends of the support elements 6 and 13 (pair 19), and 7 and 18 (pair 20), respectively upon expansion of the stent structure and subsequent pivotal movement of the support elements into the branching-off branch of the vessel. In the pivoted condition, the connecting elements 15 and 16 respectively then advantageously support the peripheral region of the vessel wall which is between the free ends of the support elements 6 and 13, and 7 and 18, respectively.

In implantation of the above-described stents, the procedure involved, with reference to FIG. 1, is preferably that described hereinafter.

Firstly, the stent 1 is positioned in the region of the vessel branching 4 in such a way that the branching portion 5 is arranged in the region of the vessel branching 4. A balloon catheter 9 with a balloon 12 is used for that purpose. That balloon 12 has two mutually separate chambers 12.1 and 12.2, between which there is an outlet opening 17, for a guide wire 8, which is guided in the catheter stem 9.1.

To assist in the positioning operation the guide wire 8 is passed through a suitable opening 17 in the region of the branching portion 5 of the stent 1 which in that case is still essentially undeformed, laterally out of the stent and into the branching-off branch 3.1 of the vessel.

Filling the chambers 12.1 and 12.2 by way of the filling openings 12.3 and 12.4 respectively in the catheter stem 9.1 with a fluid which is subjected to the action of a pressure causes expansion of the chambers and thus the stent 1, which is disposed on the balloon 12, is dilated with plastic deformation so that the stent 1 holds the vessel 3 in a permanently dilated condition after removal of the balloon 12.

After that expansion of the casing 2 of the stent 1, the support elements 6 and 7 are pivoted by means of the guide wire 8 in the direction of the arrows 10 and 11, respectively, radially out of the peripheral surface 2.3, with plastic deformation being involved in that case, into the branching-off branch 3.1 of the vessel in order to support the wall of the vessel in the region of the vessel branching 4.

It wilt be appreciated, however, that the stent according to the invention can also be implanted in another way, in particular using a balloon catheter of another configuration, with the result of providing very good support for the vessel transition.

The invention is not limited in terms of implementation thereof to the above-specified preferred embodiments. On the contrary, a number of alternative configurations are possible, which make use of the illustrated structure even in configurations of a basically different kind.

What is claimed is:

1. A stent for implantation in the region of a vessel branching, comprising:
a tubular casing with a proximal and a distal end, and defining a peripheral surface, wherein in an implanted condition the proximal end is arranged in proximal relationship with the vessel branching and the distal end is arranged in distal relationship with the vessel branching, the tubular casing including:
at least one branching portion arranged at the peripheral surface of the casing, and which is provided to open a passage into a branching-off branch of the vessel branching, and which in the implanted condition is arranged in the region of the vessel branching, wherein the branching portion includes:
first and second support bars, and
four support elements, which are provided for supporting a vessel transition, and which are bendable substantially radially out of the peripheral surface, and wherein each support element extends from a different direction into the branching-off branch, wherein the four support elements are arranged as two support element pairs, and wherein each support element pair comprises two support elements in longitudinal adjacent relationship, each support element including:
an elongated hairpin body having a bend region and first and second limbs each having first and second ends,
wherein the bend region is directed to the center of the branching portion and the first and second limbs are extended substantially in a longitudinal direction along the stent,
whereby one end of the first limb is connected to the bend region and one end of the first limb is connected to a support bar, and
whereby one end of the second limb is connected to the bend region and one end of the second limb is connected to the second limb of the elongated hairpin body of the second support element in the support element pair,
wherein the elongated bodies of the support elements are bendable at any point substantially along the length of the elongated body so that at least a portion of the elongated body is bent outward, such that the dimensions of the passage opened by the branching portion may be varied to correspond to the dimensions of the branching-off branch.

2. A stent as set forth in claim 1 wherein the support elements are of such a configuration and arrangement that in the implanted condition with the support elements bent radially out of the peripheral surface to support the vessel transition, the branching portion opens a passage in the peripheral surface which is substantially adapted to the contour of the vessel transition.

3. A stent as set forth in claim 1 comprising a plurality of branching portions.

4. A stent as set forth in claim 3 wherein at least a part of the plurality of branching portions is arranged in an annular configuration in the peripheral surface of the casing.

5. A stent as set forth in claim wherein the branching portions are arranged in immediately mutually adjoining relationship in an annular configuration in the peripheral surface of the casing.

6. A process for implanting a stent as set forth in claim 1 wherein the support elements are bent radially out of the peripheral surface into the branching-off branch after expansion of the casing by an actuating means which is moved to the branching portion.

7. A process as set forth in claim 6 wherein a guide wire provided for positioning the stent prior to expansion is used as the actuating means.

8. A process as set forth in claim 7 characterized in that a balloon catheter is used to expand the stent, which balloon catheter has at its distal end a proximal balloon and spaced therefrom a distal balloon, and between which proximal and distal balloons the guide wire forming the actuating means issues from the catheter.

* * * * *

UNITED STATES PATENT AND TRADEMARK OFFICE
CERTIFICATE OF CORRECTION

PATENT NO. : 6,579,309 B1
DATED : June 17, 2003
INVENTOR(S) : Hartmut Loos and Curt Kranz It is certified that error appears in the above-identified patent and that said Letters Patent is hereby corrected as shown below:

Column 8,
Line 35, after "claim" insert -- 4 --.

Signed and Sealed this

Fourth Day of November, 2003

JAMES E. ROGAN
*Director of the United States Patent and Trademark Office*